(12) United States Patent
Franco

(10) Patent No.: US 12,178,578 B2
(45) Date of Patent: *Dec. 31, 2024

(54) URODYNAMIC DEVICE AND PROCEDURE

(71) Applicant: Franco Intelligent Agent Solutions, Flint, MI (US)

(72) Inventor: Israel Franco, Chappaqua, NY (US)

(73) Assignee: Franco Intelligent Agent Solutions, Flint, MI (US)

( * ) Notice: Subject to any disclaimer, the term of this patent is extended or adjusted under 35 U.S.C. 154(b) by 246 days.

This patent is subject to a terminal disclaimer.

(21) Appl. No.: 17/881,894

(22) Filed: Aug. 5, 2022

(65) Prior Publication Data

US 2022/0400997 A1 Dec. 22, 2022

Related U.S. Application Data

(63) Continuation of application No. 16/472,002, filed as application No. PCT/US2016/060241 on Nov. 3, 2016, now Pat. No. 11,484,236.

(60) Provisional application No. 62/261,863, filed on Dec. 2, 2015, provisional application No. 62/250,344, filed on Nov. 3, 2015.

(51) Int. Cl.
*A61B 5/20* (2006.01)
*A61B 5/00* (2006.01)
*A61B 5/03* (2006.01)

(52) U.S. Cl.
CPC ............. *A61B 5/204* (2013.01); *A61B 5/036* (2013.01); *A61B 5/205* (2013.01); *A61B 5/6852* (2013.01)

(58) Field of Classification Search
CPC ..................... A61B 5/036; A61B 5/20–205
See application file for complete search history.

(56) References Cited

U.S. PATENT DOCUMENTS 11,484,236 B2 * 11/2022 Franco ................. A61B 5/204
2003/0171692 A1 * 9/2003 McMorrow ........... A61B 5/205
600/561

* cited by examiner

*Primary Examiner* — David J. McCrosky

(57) ABSTRACT

A method performed by a computer correlates vesicoelastic pressure data with volume data and calculates vesicoelastic work performed by the bladder, wherein the amount of vesicoelastic work performed by the bladder is determined by calculating an area under said vesicoelastic pressure data when said vesicoelastic pressure data is correlated against the volume data.

20 Claims, 8 Drawing Sheets

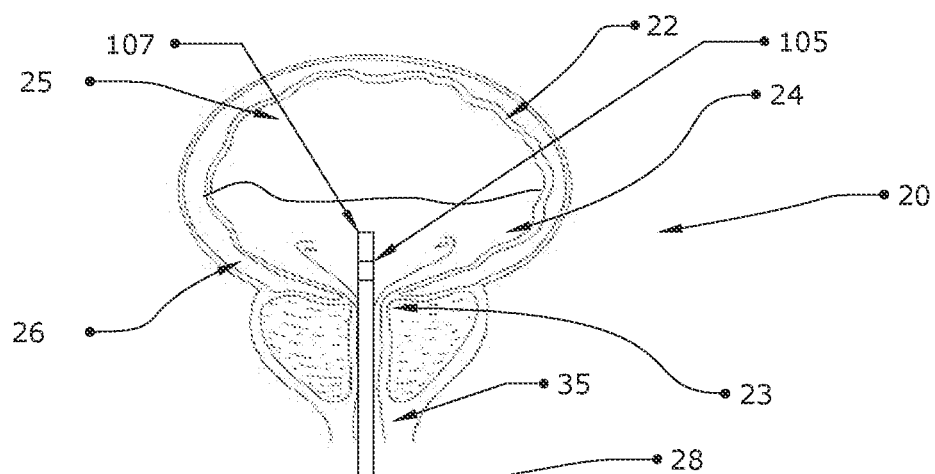
FIG 2
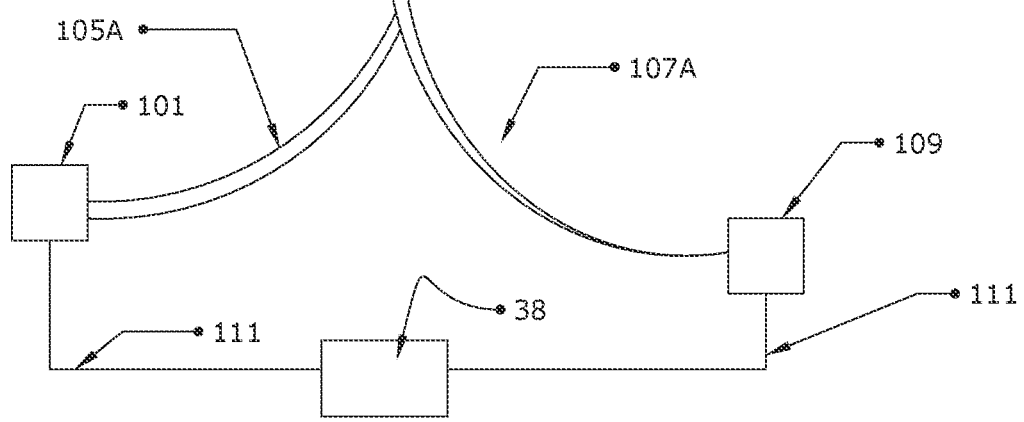

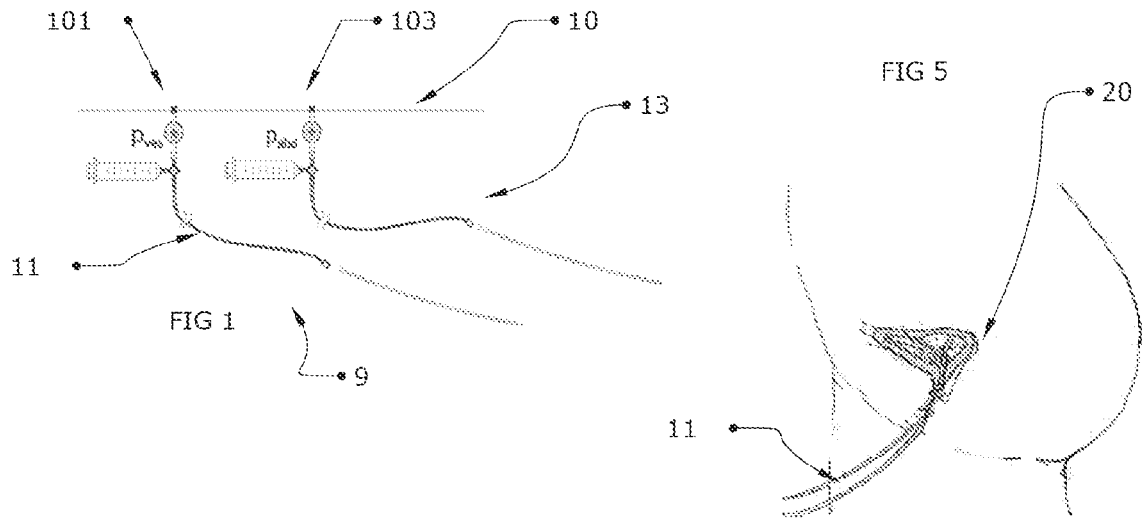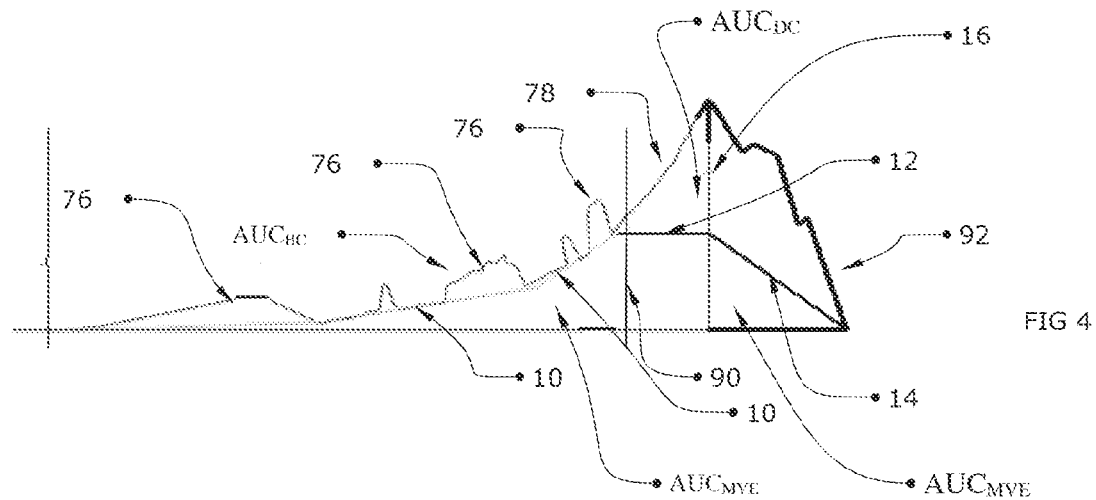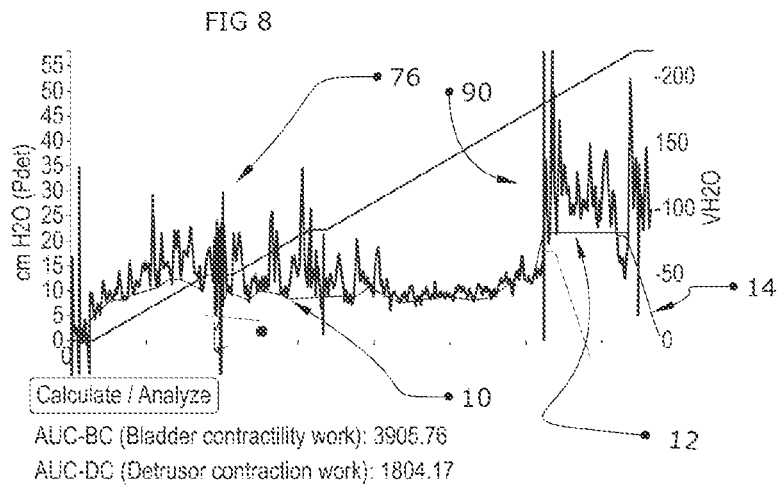

URODYNAMIC DEVICE AND PROCEDURE

CROSS REFERENCE TO RELATED APPLICATIONS

The present application is a Utility application claims priority to U.S. patent application Ser. No. 16/472,002 filed Jun. 20, 2019 entitled URODYNAMIC AND UROFLOWMETRY DEVICE AND PROCEDURE, which claims priority to a PCT Application Number PCT/US16/60241 filed Nov. 3, 2016 entitled URODYNAMIC AND UROFLOWMETRY DEVICE AND PROCEDURE, which further bases priority to provisional application No. 62/250,344 filed Nov. 3, 2015 for a URODYNAMIC AND UROFLOWMETRY DEVICE AND PROCEDURE, and 62/261,863 filed Dec. 2, 2015 entitled URODYNAMIC AND UROFLOWMETRY DEVICE AND PROCEDURE, the entirety of the above referenced applications are hereby incorporated by reference.

BACKGROUND

Urinary tract and bladder problems are prevalent amongst men and women of all ages and throughout the world. Such aliments include overactive bladder and underactive bladder where the detrusor muscle of the bladder actuates prematurely before the bladder is filled or not enough after the bladder is filled. This may be caused by dysfunction of the detrusor muscle itself or the nerve response that triggers urination (micturition). Many other bladder and urinary tract issues exist as well. Pharmaceutical companies and medical device companies have invested in and developed an array of drugs and products to diagnose and treat these issues.

On the pharmaceutical side of the industry, various companies offer prescription drugs designed to counteract the abnormal behaviors of the bladder. Likewise, medical device companies provide various products such as catheters and others designed to be used in urodynamic studies. The use of these products aid physicians and clinicians in the identification and treatment of bladder related issues.

Notwithstanding the investment, pharmaceutical and medical device companies have encountered many difficulties in defining quantifiable objective criteria to determine that treatment is effective. Present parameters that are readily available for use today such as compliance and measuring uninhibited bladder contractions are routinely open for subjective interpretation and prone to inter and intra rater variability even within the same sample at different times. This renders these criteria less than perfect for clinical practice and for clinical trials.

Conventional urodynamic principles for identifying bladder issues involve filling the bladder with a solution such as a saline solution while measuring pressure vs. time while the bladder is being filled. A catheter is inserted through the urethra and into the bladder (see FIG. 5 for example) and the saline solution is passed through the catheter. The pressure is measured by the catheter through a pressure sensor either built into the catheter or measured as transmitted pressure in a pressure sensing module outside the patient. External software charts this pressure versus time. The output from the catheter is graphed and a physician then inspects the graph to qualitatively analyze the pressure variations over the time scale associated with the fill to visually guestimate whether fluctuations in pressure indicates an abnormal bladder condition or whether treatment is effective. The methodology, in some instances, involves the physician using calipers to painstakingly, physically measure spikes in the graph. Compliance is measured manually and the location of the maximal volume and pressure is eyeballed to represent the place most likely to have been not associated with a detrusor contraction. These processes can be long and uncertain. Likewise, in drug trials, the same procedure is used over multitudes of different graphs from numerous patients to, again, guestimate the efficacy of a particular drug to a bladder problem. The present invention was developed in light of these and other issues.

BRIEF DESCRIPTION OF THE DRAWINGS

FIG. 1 is a schematic view of a system for performing a urodynamic procedure according to one aspect of the invention;

FIG. 2 is a schematic view of a system for performing a urodynamic procedure according to one aspect of the invention;

FIG. 4 is a schematic view of a urodynamic system according to an aspect of the invention;

FIG. 5 is a graphical view of a pressure versus volume curve for one aspect of the invention;

FIG. 8 is a graphical view of a pressure versus volume curve for one aspect of the invention;

DETAILED DESCRIPTION OF PREFERRED EMBODIMENTS

Figure 3A:
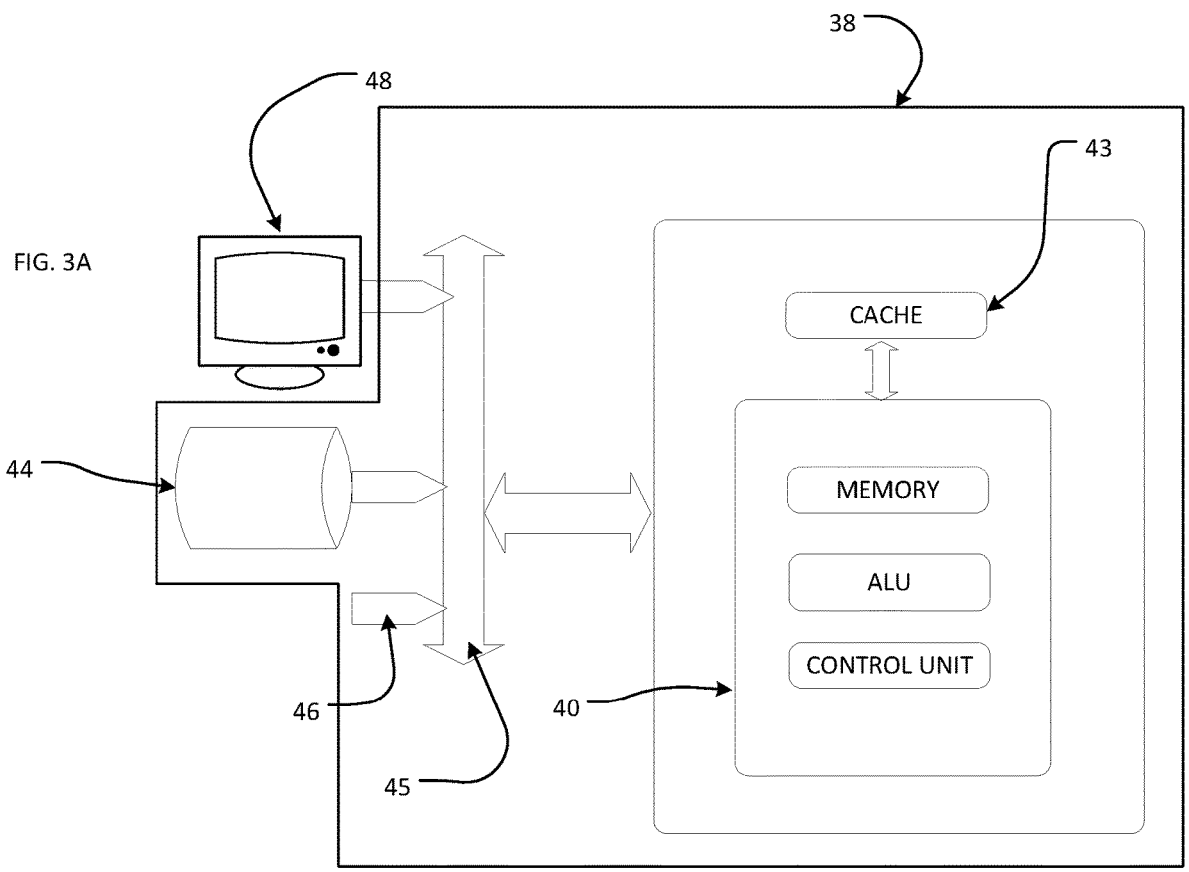
FIG. 3A is a schematic view of a system for processing data according to an aspect of the invention.

Referring now to FIG. 1, an embodiment of a device and procedure for conducting urological testing according to one aspect of the present invention is shown and described. In FIG. 1, a urological testing system 9 is shown including a bladder catheter 11 and a rectal catheter 13 connected respectively to pressure transducer 101 and pressure transducer 103 respectively. The bladder catheter, in one embodiment, pumps a saline solution generally the same in concentration and composition to that of rectal catheter.

However, one skilled in the art will recognize alternate fluids that may be used instead of the saline solution described herein.

Referring now to FIG. 2, the application of the urological testing system 9 to a bladder 20 will now be shown and described. Bladder 20 is shown having a catheter end 28 inserted therein. The catheter end 28 is inserted through the urethra and into fluid communication with the interior cavity 25 of the bladder 20. Physiologically, the described bladder is a human (male or female) bladder but also may be that of an animal. The bladder 20 generally includes bladder walls 22 that define the cavity 25. A detrusor 26 is a muscle encircling the bladder walls 22 that actuates to constrict the bladder walls when an amount of urine in the interior cavity 25 reaches a predetermined pressure sensed by nerves surrounding the bladder walls, resulting in release of the interior sphincter muscle 23 and external sphincter muscle 35 to result in urination or micturition to expel the urine in the cavity 25 through the urethra.

With continued reference to FIG. 2, the catheter end 28 is generally a dual channel cylindrical element that includes a pressure sensing channel with an exposed region 105 and a channel with an opening 107 for infusion of liquid 31 therein. The catheter includes channel 105A that, at one end, connects to exposed region 105 and, at a second end, connects to pressure transducer 101. The pressure sensor may also be provided in a separate channel at the tip of the catheter. In the present embodiment, the bladder catheter 11 is part of the catheter end 28 such that the saline solution flows through a passage in the catheter end 28 and into the bladder 20 during fill.

The catheter in the present embodiment includes a second channel 107A that connects opening 107 to pump 109 such as a centrifugal pump. Pump 109 is fluidly connected to the previously mentioned saline solution and acts to pump the solution through the second channel 107A, through the opening 107 and into the bladder during the procedure.

The pressure transducer 101 can be any standard pressure sensor such as those employing a diaphragm positioned between a vacuum or known pressure and the saline solution in the bladder. In one aspect, a piezoelectric generated output voltage is created based on the deflection of the membrane against a piezoelectric element. The pump 109 in one embodiment is a scaled or calibrated pump that outputs a signal through lead 111 to computer 38 representing the volumetric flowrate of saline into the bladder. However, instead of a calibrated pump, a separate volume sensor, in one embodiment, is in the form of a volumetric flow sensor that measures the flow rate of fluid through the aperture in the second channel 107A and reports that value to a processing device or the computer to associate that flow with a time scale and calculate the volume per unit time. In another aspect, the cross section of the aperture in the second channel 107A or the opening 107 is known and the pressure can be used to calculate flow rate. One skilled in the art will recognize other means for calculating volume and flow rate.

The pressure sensor and the volume sensor provide an analogue output signal to the signal line 111 that, in turn, feeds to analog to digital or A/D converter in computer 38. The A/D converter converts the analogue output to digital and provides that digital signal to computer 38. It is also recognized that computer 38 may receive the analogue signal and convert it internally to a digital signal through an appropriate I/O port and drivers.

Figure 11:
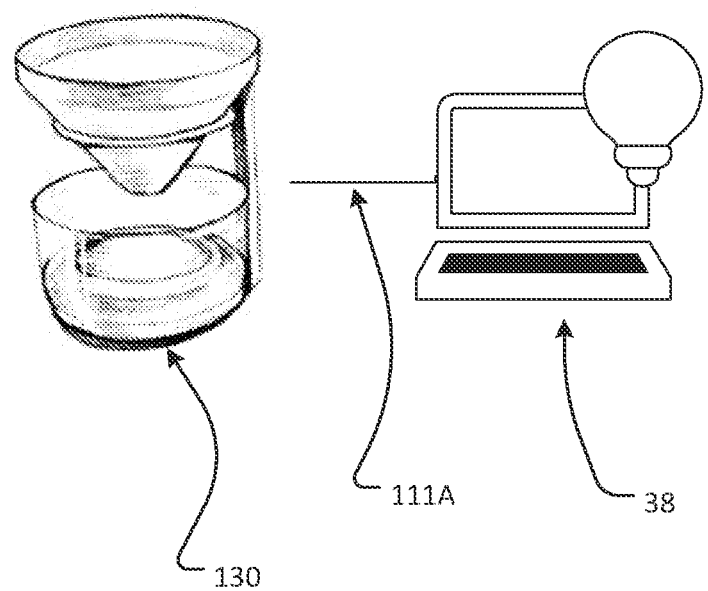
FIG. 11 is a schematic view of a system for performing a urodynamic procedure according to one aspect of the invention.

With reference to FIG. 11, to calculate volume during voiding (when the patient is expelling urine instead of during filling of the bladder), a uroflow voiding device 130 is used. The uroflow voiding device 130 is connected to computer 38 by the data line 111A to similarly provide data representing the volumetric flowrate exiting the bladder during voiding or micturition. If one knows the starting volume in the bladder, the volumetric flowrate can be used to calculate current volume of the bladder at a particular time or at a particular pressure in the bladder. The system shown in FIG. 11 may be replaced by any known volumetric flowrate system, such as a catheter inserted into the patient, that measures the flowrate of urine being expelled from the bladder.

Computer 38, in one aspect, employs a timing or synchronizing feature or other methodology to be used to coordinate the pressure, volume of the bladder and time components such that the pressure and volume can be associated with or charted against a time scale of the fill. In another aspect, the pressure is correlated with or charted against (i.e. the pressure at each volume point during fill) the volume of the bladder as shown in FIG. 4. In one example of the present invention, once voiding begins or micturition starts at line 90, then the system may be paused while the patient is connected to the system of FIG. 11. Or, the patient is switched to the system of FIG. 11 once the urge to urinate begins. Thereafter, the process resumes and the pressure is measured against the volume or time as desired as the volume reduces or time passes. For example, with reference to FIG. 9, the volume increases as shown by arrow 122 until reaching line 120. Line 120 can be at a point at or to the right of line 90 or generally left of the max pressure and represents the beginning of micturition or when the patient has the urge to urinate. The pressure increases with actuation of the detrusor and then voiding begins and the volumetric flowrate is measured by the system of FIG. 11 until reaching zero. By knowing the volumetric flowrate from the measurement, the volume of the bladder is calculated at each point of time and correlated to the pressure at that time/volume. By this way, the volumetric flowrate, time, volume and pressure can all be correlated and thereby charted.

It will be understood that any known urological testing may be undertaken with the present invention and the described embodiments are not limited to the specific testing described herein. Additionally, instead of real time data provided to the computer 38 during testing, the present invention may be used with data files from previously undertaken urological testing, whether in graph or data format that are later uploaded through any known means to computer 38.

In the same fashion described with respect to the bladder, it will be understood that rectal pressure and time may also be obtained in the rectum for reasons that will be described. The pressure is provided from a catheter end in the rectum in a similar way to the computer 38. As will be discussed later, the use of the rectal pressure is used in combination with the bladder pressure to obtain a true bladder pressure.

Referring now to FIG. 3A, computer 38 is described in greater detail. In one embodiment, computer 38 is a conventional computing system that includes a main processor 40 with an arithmetic logic unit, control unit and memory and a cache memory 43. A data bus 45 provides a plurality of I/O ports that connect display 48 and main memory 44. The display may be a LCD, touch or other display. I/O port 46 is for receiving either analogue information from signal line 111 and 111A.

Figure 3B:
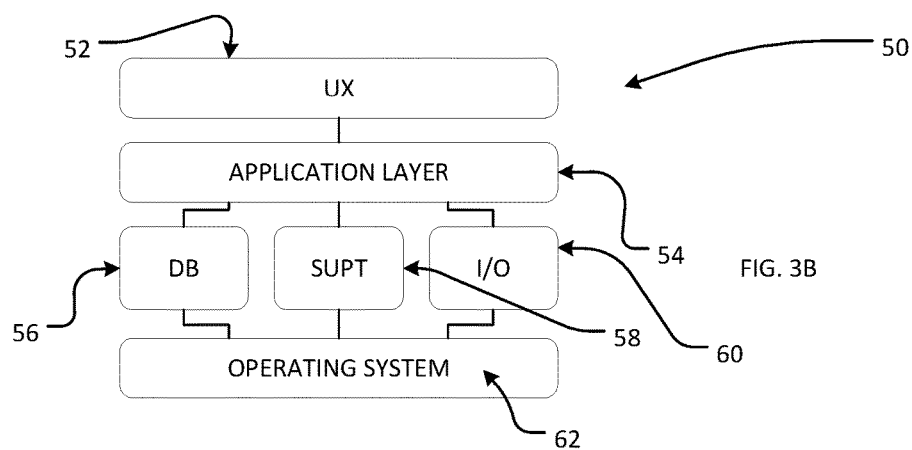
FIG. 3B is a schematic view of a system for processing data according to an aspect of the invention.

Software operating in computer 38, in one aspect, is described with respect to software stack 50 in FIG. 3B. Software stack 50 includes a user interface or UX 52 that is a rendered image providing results of the analysis, input and output features for entering requisite information into the program that may be entered by a user or physician. The UX may be a PC or mobile platform UX (connecting to a server through web APIs or other means). An application layer 54 is provided that does high level processing and normalization of data, sending and receiving data and communicating with the UX 52. Application layer may be provided through client side or a combination of client and server side application and scriptin, on premise or cloud based. Database 56 is any standard database (SQL, Oracle or others) that maintains data in a tablature format, provides data modeling and retrieval capabilities. Libraries and support programs 58 provide additional support, analytics, data mapping, graphing and math functions or other libraries and functions as required or called by application layer 56. I/O 60 provides drivers and other software needed to communicate, convert or otherwise recognize data provided to computer 38 (such as pressure or volume data) as well as outputs to controllers or other peripherals such as the display. Finally, operating system or OS provides all needed operating system functions as required.

With continued reference to the figures, one embodiment of the operation of the present invention is shown and described. A physician or assistant thereto injects the saline solution from bladder saline container 15 into bladder 20 through the catheter 11 and catheter end 28 as previously described. Likewise, saline solution from the rectal catheter is injected into the rectum of the patient. The bladder 20 is filled with saline 24 at a continuous rate (i.e. 10 cc/min) in one example. The bladder pressure is referred to as the vesical pressure and the rectal pressure is termed the abdominal pressure. The subtracted pressures of vesical minus abdominal are termed the detrusor pressure or the actual pressure of the bladder. The bladder is filled until micturition occurs or until pain is experienced by the patient or unsafe bladder pressures are reached. Such pressure is charted against volume both during filling and voiding.

Work in thermodynamics for a closed cavity is represented by dw=Pdv. Thus, the change in work is equal to the pressure times the change in volume. Accordingly, the inventors have determined that the work done by a bladder (or done when filling or voiding the bladder) is equal to the mathematical integral of the aforementioned equation or otherwise stated $W=\int_0^V Pdv$ where V is the final volume and P is the pressure for each delta V. Further, the inventors have determined that such work at various sections of a P v V (pressure v volume) curve may result in improved and more quantitative means for determining whether the detrusor muscle is actuating too frequently, for example, which would be represented by an increased amount of work or, in the case of underactive bladder, where the detrusor muscle is not actuating enough at certain stages (such as during micturition). This means that if one is to plot the pressure vs the change in volume, the work done by the bladder is the area under that curve or $\Sigma p \times v$ where for each volume point along the fill. Linearly, this can also be written as $c \times \Sigma p \times t$ where c is a constant that converts the linear time value into the volume value (say by knowing the constant volumetric flowrate of the pump 109). Therefore, one aspect of the present invention is to determine the work done by the bladder from the area under a pressure vs. volume curve (hereinafter referred to as a urodynamic curve) and use that work to determine abnormality of bladder functions.

In FIG. 4, the AUC (area under curve) is shown with respect to one example urodynamic curve. The urodynamic curve is representative of a bladder and the area under the curve (AUC) is proportional to the total work being performed by the bladder. In the graph of FIG. 4, the X axis represents change in volume as the bladder is filled while the Y axis represents the bladder pressure exerted at the various points during the fill and subsequently during voiding.

With continued reference to FIG. 4, another aspect of the present invention is the ability to delineate different components of a urodynamic curve. More specifically, the urodynamic curve is broken up in areas representing different phases of bladder activity during urological testing. As such, the inventors have recognized that the amount of work done at various sections of the P v V curve relate to different bladder dysfunctions. Generally speaking, in healthy bladders, the pressure during the initial phase of the fill is generated by elastic characteristics of the bladder. Later, the detrusor activates and the bladder pressure is a function of both the detrusor and the elastic characteristics. Accordingly, the present invention in one aspect breaks up the urodynamic curve up into several components that represents when only the elastic conditions should occur and when the detrusor actuates. Therefore, different forms of work done are measured by measuring the area under the curve (AUC) at different regions along the curve.

When the detrusor actuates, the amount of work AUC DC represents whether the detrusor is providing sufficient force to expel urine or whether there may potentially be an underactive bladder condition. AUC MVE represents the vesicoelastic conditions of the bladder and whether there is sufficient rigidity in the bladder to exert elastic expulsion of the urine. Abnormally large amounts of work may represent blockages or other impediments to urination. Dividing the total work by the total change in volume provides a representative average pressure exerted or seen by the bladder. Such division by total volume can also be applied specifically to the AUC MVE to understand the average pressure from the vesicoelastic region, the AUC DC to understand the detrusor average pressure or the total of the two to understand the average total pressure exerted during this phase.

More specifically, an elastic component, collagen and muscular component in the bladder walls (and muscle tissue of the detrusor) combine to form a combined component that will be defined as the Muscular and Vesicoelastic (MVE) component in the present invention. The MVE component relates to the elastic characteristics of the bladder. Therefore, the AUC of this portion of the curve is the vesicoelastic power or work performed by the elastic, collagen and muscle fibers in the bladder. In healthy bladders, this component makes up the filling phase prior to a detrusor 26 contractions that occur once the volume in the bladder reaches a certain amount. The muscular vesicoelastic component is defined to have reached its maximum exclusive of any contractions of the bladder where lines 10 and 12 meet. At line 12, the vesicoelastic component remains stable and constant (applying approximately the same pressure) while the bladder either begins expelling urine or continues to increase in volume slightly until the sphincter opens at which point micturition occurs. During this phase and after actuating the detrusor, the pressure approaches its peak contraction pressure (line 16) and then it decays (line 14 shows the vesicoelastic component and line 92 represents the detrusor+the vesicoelastic portion) after opening of the sphincter as the bladder contractions subsides during expulsion of the fluid therein. During this last phase, the detrusor is still working against an outlet resistance and therefore work is being done at this point. The MVE component is represented by line portions 10, 12 and 14 in FIG. 5 where the line 10, 12 and 14 demarcates detrusor bladder contractions (above the line) from the MVE component (below the line). The lines illustrating this point of demarcation increase (line 10) during initial fill and then flatten (line 12) where the detrusor activates up to the peak of the contraction which is depicted by line 16. From line 16, the muscular viscoelastic component shown by line 14 decays as tension in the bladder degrades with the contraction (segment 3) of the bladder during expulsion of the fluid from the bladder.

Some pressure v volume curves continue to show the volume increasing even after micturition occurs. This is a function of the graph being generated as a function of time and then being converted to volume based on the constant multiplied for the volumetric pump. For purposes of understanding, the volume is reversed once the detrusor actuates such that the measure is the measure of voiding of the bladder. This may happen by stopping the procedure once micturition is detected or the patient desires to urinate and then connecting the patient to load cell uroflowmetry device (see FIG. 11). It can also be accomplished by combining two uroflowmetry tests (one for filling and one for voiding) or any other known means. Flowmeters can be conveniently positioned beneath a commode or free-standing to accommodate a patient's typical voiding position (see FIG. 11 for example). By this way, the volume flow rate of urine exiting the patient's bladder can be detected and, as discussed previously, the pressure in the bladder may be measured and plotted there against. The result is the graph shown in FIG. 4 to the right of line 90 that charts pressure against a reducing volume during voiding.

Each of the line portions 10, 12 and 14 is illustrated as if it were a Hookian linear relationship even though it is understood that there is some non linear degradation due to the nature of the bladder and its elastomer characteristics. Accordingly, it is understood and contemplated by the present invention that line segments 10, 12 and 14 may be illustrated as nonlinear to reflect this relationship. Accordingly, the area under the curve between zero pressure and lines 10, 12 and 14 is depicted in FIG. 2 as $AUC_{MVE}$ and generally represents bladder compliance or work done by the MVE component of the bladder.

$AUC_{BC}$ is the area bounded by lines 10 and line 76 during the initial fill phase prior to normal actuation of the detrusor in response to reaching the threshold volume to cause expulsion. The work performed here is due to detrusor (bladder contractions which are occurring spontaneously and not generating enough force to empty the bladder). These are commonly called uninhibited contractions and are an important feature that the present invention identifies for accuracy of medical drug trials and to measure the efficacy of medications and treatments that involve the bladder and the elimination of detrusor contractions.

$AUC_{DC}$ is the area bounded by the line portion 12 and line 76. This represents the detrusor contractions that are used to empty the bladder. The area below the line portion 12 in this figure is the $AUC_{MVE}$ and above it is the work being used to empty the bladder by the detrusor ($AUC_{DC}$).

Total work done by the bladder is $AUC_T = AUC_{MVE} + AUC_{BC} + AUC_{DC}$. A ratio or percentage would be calculated for each of these component such as:

$$\frac{AUC_{VE}}{AUC_T} + \frac{AUC_{BC}}{AUC_T} + \frac{AUC_{DC}}{AUC_T} = 1$$

Figure 6:
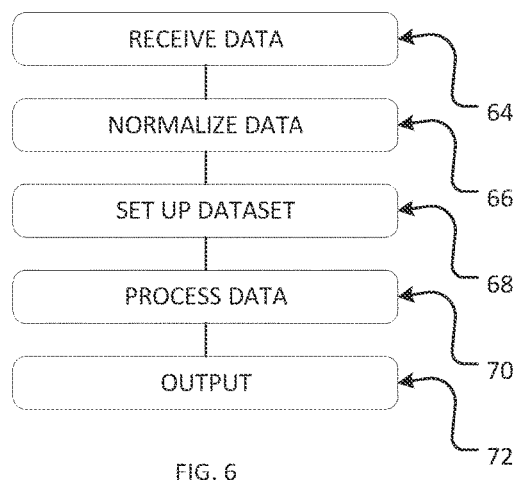
FIG. 6 is a flowchart according to an aspect of the present invention.

Referring now to FIG. 6, a process is depicted for execution by computer 38 and software stack 50 to obtain the AUC values for a urodynamics curve and present those results to provide a meaningful output representing characteristics of a bladder in a quantitative way. In FIG. 6, the process begins in step 64 by the computer 38 receiving data from catheter end 28 as discussed previously. The data can be received directly by I/O 46 through a serial, USB or other port or can be loaded either manually or automatically as a file such as flat text file. Data formatting can be in any known way. In one example, the file is in the form of a CSV, TSV OR TXT file. The file may be uploaded and stored via an uploader on the UX that pulls the files stored from memory or a real time port connection to the catheter end for real time processing.

In step 66, the data received in the previous step is normalized by application layer 54 to ensure it is in proper and consistent format so that it can be processed by the application layer 54. In step 68, the data is then loaded into an array type element, database tables, other data model or some other means that is formatted to readily make each pressure and volume and associated time value available for the desired processing. The data may either reside in volatile memory 43 or in a database in memory 44 so that it can be recalled or invoke additional data processing features. In one aspect, the data model correlates the retrieved pressure values with the corresponding volume and time values so that each pressure point is known for its corresponding time and volume point. In step 70, the data in the data model is then processed by the application layer 54.

Figure 7:
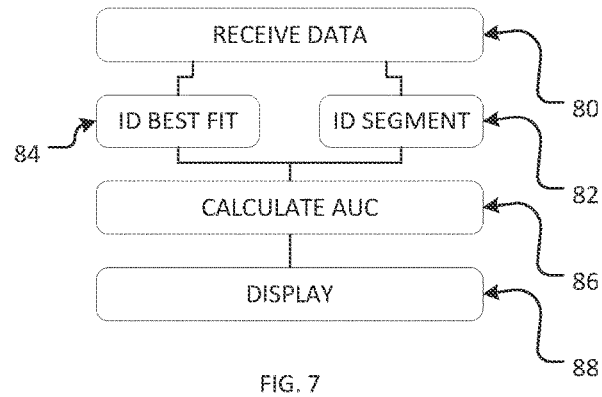
FIG. 7 is a flowchart according to an aspect of the present invention.

Referring now to FIGS. 7 and 8, the processing in step 7 will be described in greater detail. In step 80 of FIG. 7, the maximum pressure value is identified through comparison of all pressure values received and referenced or stored. The pressure values may be smoothed or processed to ensure no unusual values throw calculations off. This can be accomplished through a number of means including a comparison of all the pressure values to identify the maximum. This maximum value corresponds to the pressure at line 16 in FIG. 8. In step 84, linear regression is then used to identify a best fit line that resides at the bottom points of the pressure values that were stored in the data model. The data points associated with this best fit line are also stored in the data model. The best fit line is denoted in FIG. 8 as line 10 (corresponding to line 10 in previous FIGs). By adjusting the best fit line to fit the lower points of the pressure fluctuations and to filter for unusual downward or upward spikes, the generated line 10 closely resembles the vesicoelastic characteristics of a normal bladder (without the detrusor spikes where the detrusor actuates prematurely during filling) during the fill phase. As such, the application layer 54 employs the processor 40 to, different from standard regression, provide a line fitting the bottom points of the graphed data and not just the midpoints of the graphed data. For example, the line 10 reflects what the bladder should be doing prior to micturition if there was not premature detrusor activity occurring. The best fit line 10 extends to detrusor line 90. In one aspect, movable points are positioned along the line 10 to allow a physician or expert to adjust the line 10 to best suit such expert's understanding of how the line 10 should look and to best fit the data given the spikes and their expert opinion in the matter. For example, points movable through click events can be dragged and dropped to different positions to change the line to better reflect the vesicoelastic conditions. This can be accomplished through scripting in the rendered view in the UX through, for example, javascript or D3 to permit adjustment of the rendered image and post back to the server to recalculate values to be discussed below.

Detrusor line 90 is represented in the figure as a point along the volume data where transition from line 10 to 12 occurs. The initial location is arbitrary by placing it at a point that likely corresponds to this point. Alternatively, the software looks at the slope of the generated line 10 and identifies an increased slope or spike at a later position along the volume curve and determines that this is where micturition or detrusor actuation occurs. Alternatively, the line can be set if the data is being collected real time when the testing switches from filling to voiding. As will be described later, the line is movable to permit adjustment by a physician to permit the physician or user to adjust the line left or right depending on where the user visually identifies the correct position to be.

Data points associated with line 12 are then generated by connecting the intersect of detrusor line 90 with the best fit line 10. The data points associated with line 12 are those of a constant pressure value that extend to the volume point associated with line 16 (max pressure). During this period, the vesicoelastic forces are largely constant while the detrusor forces are responsible for the increase in pressure. Once max pressure is achieved and begins to reduce, the vesicoelastic forces are largely reducing in a linear fashion until reaching zero. Thus, data points for line 14 are generated by connecting the datapoints at the end of line 12 with the zero pressure reading at the end of the curve. All of the previously mentioned values associated with the aforementioned lines are generated and stored in the data model for subsequent use by the program.

Next, in step 86, all the AUC values are calculated by pulling the various data points from memory 44 or 43 and calculating the AUC through known numerical analysis methods. More specifically, the AUC for lines 76, 10, 78, 92, 12 and 14 are calculated and stored. The data for lines 10, 12 and 14 are, in one embodiment, that which was posted back after adjustment by the user or physician in the UX 52. Thereafter, the work performed by the detrusor is calculated in two parts. First, the $AUC_{BC}$ is calculated by subtracting the summation of the pressures of line 10 from the summation of pressures for line 76. Next, $AUC_{DC}$ is calculated by (AUC Line 78–AUC Line 12). By this way, the work done by the detrusor prior detrusor actuation and during detrusor actuation (and during micturition) is calculated.

In step 88, the results are displayed to the UX 52. Here, in one example, a page is rendered that presents the data in the format as shown in FIG. 8 which includes the rendered graph of P v V, and the corresponding calculated and actual values as well as the various AUC calculations.

In the display depicted in FIG. 8, slider bar 90 is movable left and right by a user's interaction (via mouse). Similar to that described above, in one aspect, this may be accomplished through scripting on the client side with post back data to the server side for calculations by the application layer 54. In response to this, the AUC values are recalculated to account for the new position and intersection of the slider bar 90 with the best fit line. This permits a medical practitioner to visually identify where he or she believes that the line should be located where detrusor actuation begins.

Accordingly, a user such as a physician is able to load urodynamic studies into the presently described system and obtain the amount of work generated in the BC phase during fill. As a result, one obtains a quantitative determination of the detrusor work performed during this BC phase thereby providing the physician or user a quantitative means for determining how much the detrusor actuates before it reaches micturition. For example, if the BC work is relatively low, the physician may determine that the bladder is acting relatively normal. Likewise, if the amount of work done during this phase is large, the physician may conclude that the patient is suffering from overactive bladder and can prescribe medication or other treatments. Similarly, during drug trials, the physician may treat a patient with a particular medication, say Botox, and measure the difference in work performed during this phase before and after treatment. The result is a more quantitative means of determining dysfunction and treatment.

In another aspect, the present invention can be used to determine bladder dysfunction during the micturition phase. For example, the present invention may be used with respect to underactive bladder. Here, the total work is determined (AUC MVE+AUC DC) to obtain the total work done by the bladder during voiding. This total work takes into account both vesicoelastic and detrusor contractions. This value is then divided by the total change in volume from line 90 to the end of line 92. This represents the total AUC (Work) divided by the total change in volume which equals average pressure during voiding. The present embodiment uses an average pressure, instead of a peak pressure, to determine whether the detrusor is not actuating properly. As such, the present inventors have determined that the use of an average volume may be more representative of actual issues as it takes into account pressure over change in volume or time. Such average pressure may be calculated in the AUC DC or AUC MVE phases to identify average pressures in both the detrusor and vesicoelastic regions.

Figure 9:
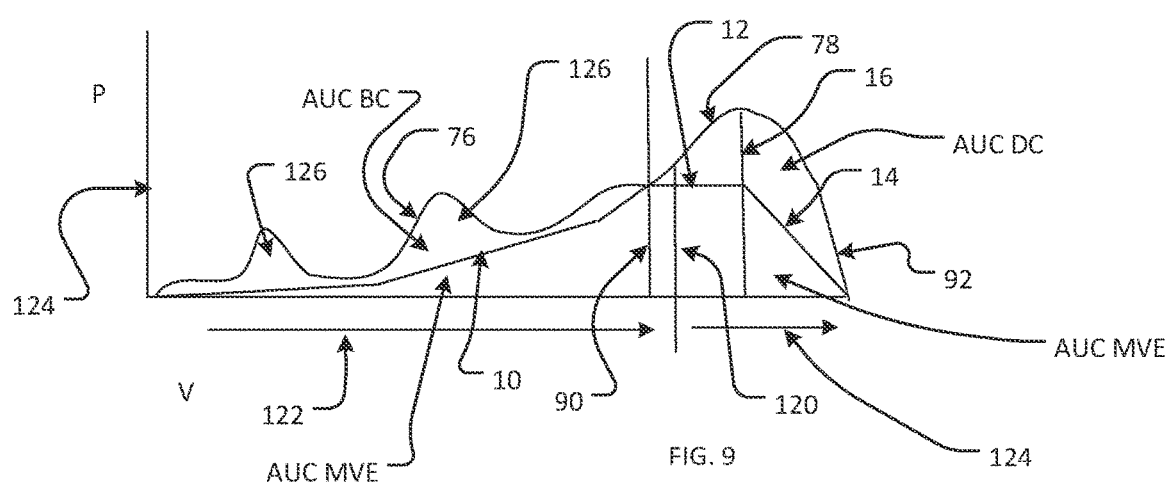
FIG. 9 is a graphical view of a pressure versus volume curve for one aspect of the invention.
Figure 10:
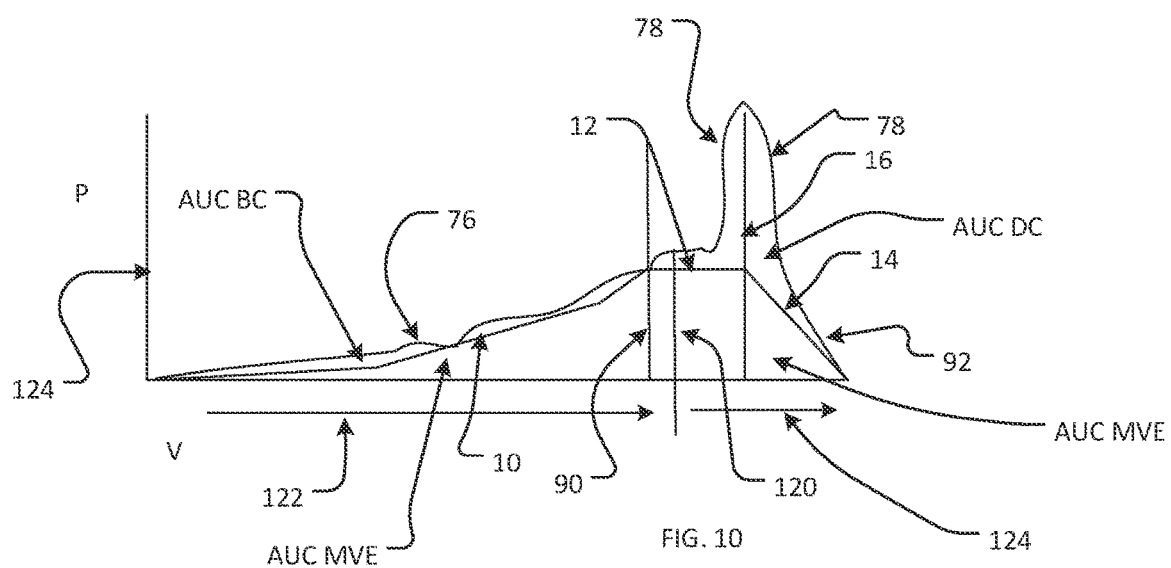
FIG. 10 is a graphical view of a pressure versus volume curve for one aspect of the invention.

Referring now to FIG. 9, an illustration of the urodynamic curve is shown and described. In FIG. 9, line 76 is shown having bumps 126. These represent detrusor contractions occurring prior to micturition or line 90. In FIG. 10, line 76 is shown without having similar bumps therein. As will be understood, the AUC BE in FIG. 9 will be larger than that in FIG. 10 is a result of these bumps 126. Accordingly, one will understand that the area under the curve where the detrusor is actuating will be larger than that where it is not.

With continued reference to FIG. 9 and FIG. 10, the total area under the curve from line 90 to line 92 represents the work performed by the vesicoelastic and detrusor components during micturition. This work divided by the change in volume from line 90 to line 92 represents the average pressure during micturition. In one example, the peak pressure in FIG. 9 represented at line 16 is smaller than the peak pressure shown in FIG. 10. However, the peak pressure in FIG. 10 is concentrated over a smaller change in volume than that of FIG. 9. As such, one may be incorrect in concluding that the peak pressure in FIG. 10, being higher, is more indicative of dysfunction in the bladder. Instead, the present invention utilizes the average pressure over the change in volume to represent an average pressure for identifying dysfunction such as underactive bladder.

In another embodiment, the data from the data model is used to calculate additional features for the understanding of the health of the bladder. In one example, the degree in spike (local pressure value relative to the best fit line is calculated for various points along the curve to identify specific fluctuations in the detrusor muscle at a local level to identify at various points during the bladder fill where detrusor contractions occur). Likewise, the catheter end itself may provide ultrasonic, electrical current or vibration or other sonic characteristics through the saline solution and the pressure or contractions can be measured to understand bladder characteristics. Also, the data model may be loaded into the database and the bladder characteristics can be stored for multiple patients to create a database of urological curves that may represent specific conditions.

Uroflowmetry is performed by measuring urine flow using various apparatus to measure flow. In one aspect, a flow meter is provided that measures the flowrate of urine or other solution exiting the bladder. The flowrate can be measured overtime. As described in previous embodiments, a flow curve is produced which is outlined by the flow rate in the y axis and time in the x axis. Again flow curves represent the principles of thermodynamics and the area under the curve is proportional to the work being performed by the bladder. These flow curves and the distinctive patterns associated with these curves such as; bell, plateau, tower, interrupted and staccato, in one aspect, are calculated and used to define certain medical conditions associated with abnormal urination. For example, in one embodiment, the flow rate loaded into the data model is then used to calculate slopes of the curve at various points during urination to determine if the detrusor or other features of the bladder are excreting at an extremely high rate.

A system to define the slope (acceleration of the initial void to the maximal flow velocity includes or initial acceleration) can be used to define these diagnostic categories especially when combined with the ability to measure the area under the curve.

Relating to FIG. 6, the uroflowmetry curves can be analyzed by drawing a line from the initiation of flow to the point of maximal flow to represent the average acceleration of fluids exiting the bladder. Another line that measures the maximal acceleration would be or can be included as well in the determinations. The area under the curve can be calculated to provide and indication of work being performed or in this case the Power of the void (power=work/$\Delta$t).

Figure 12A:
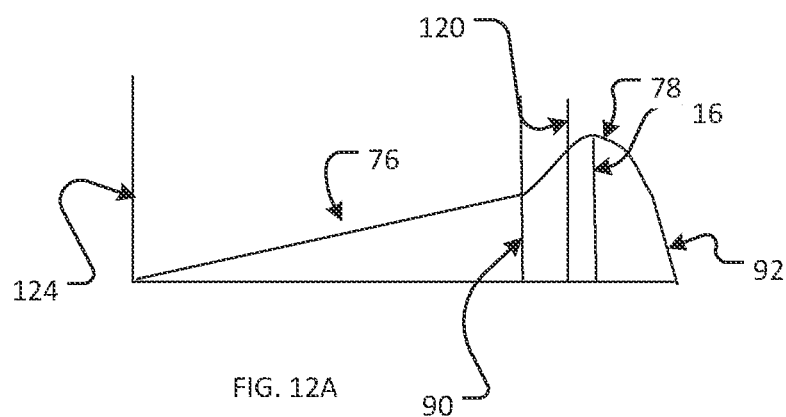
FIG. 12A is a graphical view of a pressure versus volume curve for one aspect of the invention.
Figure 12B:
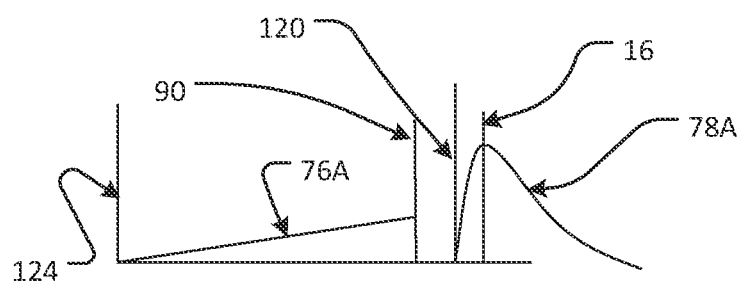
FIG. 12B is a graphical view of a pressure versus volume curve for one aspect of the invention.

Referring now to FIGS. 12A and 12B, another embodiment of the operation of data processing in step 70 of FIG. 6 is shown and described. In FIG. 12A, pressure is shown being charted against volume as described in the previous embodiments. In step 70, the power exhibited by the bladder 20 is charted against time. Here, power is equal to the pressure times flowrate (multiplied by a constant). The power shown is actually the power input into the bladder until micturition occurs. More specifically, it is the flowrate of the pump pumping saline into the bladder 20 times the pressure in the bladder 20 at each point in time. As such, step 70 uses the pressure, volume and time data to calculate the change in volume per unit time at every pressure point. FIG. 12B shows the resulting graph of this power vs time calculation. Specifically, the power steadily increases as the pressure increases at a constant flowrate (due to the constant volumetric flowrate pump) until the detrusor muscle actuates at line 90. Thereafter, the power increases as the constant flowrate pump continues to pump while the pressure increases due to the detrusor muscle as well as the vesicoelastic conditions in the bladder 20. At this point, the pump is stopped and the patient is connected to the device shown in FIG. 11 to permit measurement of pressure, volume, flowrate and time during micturition. Accordingly, micturition is shown beginning at line 120 where the power begins at zero and increases steeply to a maximum power (associated with maximum pressure in the bladder 20 and maximum flow rate of urine exiting the bladder 20) and then gently degrades as urine exits the bladder 20.

Underactive bladder or UAB is a condition associated with inability to urinate once the bladder reaches micturition pressure and volume. As such, the inventors have realized that underactive bladder may exhibit symptoms of high bladder pressure and low flow rate or high flow rate and low bladder pressure. Therefore, simply measuring pressure may not provide sufficient means to identify UAB. By using power, a calculation is provided that accounts for both pressure and flow rate. Therefore, the inventors have realized that calculation of power versus time provides a good analytical tool to identify underactive bladder as this provide an indication of both pressure and flow rate during the time span of micturition.

Figure 12C:
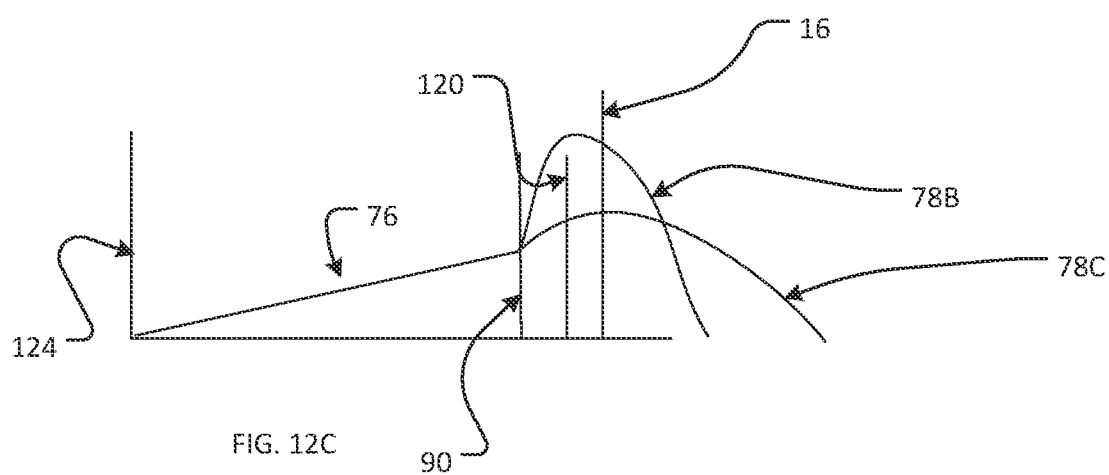
FIG. 12C is a graphical view of a pressure versus volume curve for one aspect of the invention.

For example, with reference to FIG. 12C, two different pressure versus volume curves are shown during voiding (similar to that of FIG. 12A). Curve 78B exhibits a larger pressure but a smaller change in volume while curve 78C exhibits a smaller pressure but a larger change in volume. As will be understood, either one of these curves 78B or 78C would result in the same power curve as shown in FIG. 12B as the curve in FIG. 12B is a function of both pressure and flowrate and either one of these curves might exhibit underactive bladder. Thus, comparing the power curve of the patient to a normal power curve can be used to identify flowrate and pressure symptoms of underactive bladder.

In FIGS. 13, 14 and 15A and 15B and step 70 of FIG. 6, a further embodiment of the present invention is shown and described. In the aforementioned figures, the first law of thermodynamics is used to calibrate the filling phase and voiding phase. More specifically, the energy and during filling of the bladder due to vesicoelastic considerations is equal the energy out due to vesicoelastic considerations. As such, by calculating the energy in during filling, this value can be subtracted from the energy out to compensate for differing physiological characteristics of the patient.

Figure 15A:
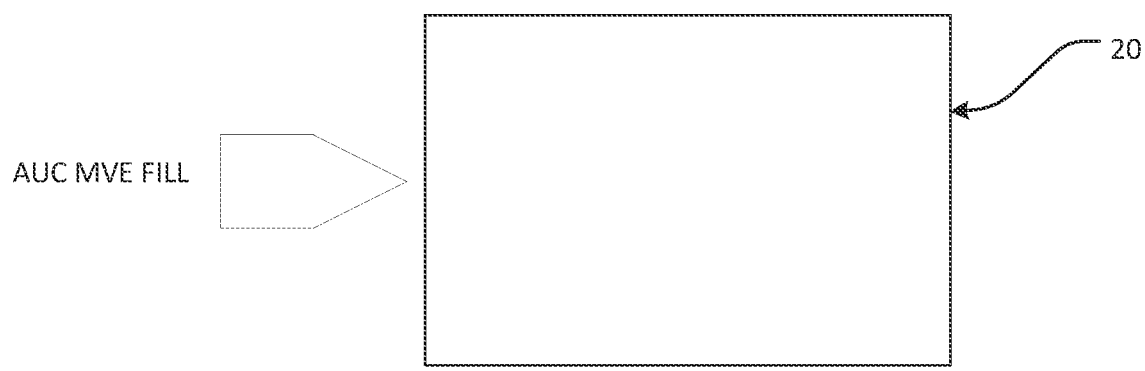
FIG. 15A is a schematic view of a bladder according to an aspect of the present invention.
Figure 15B:
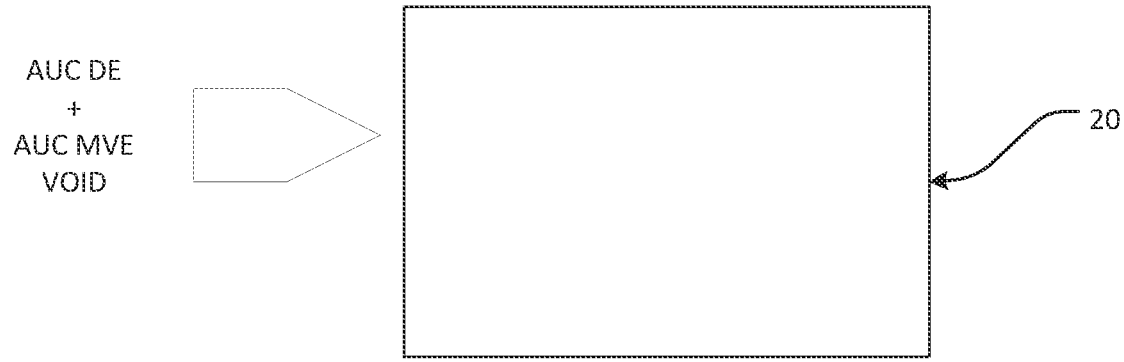
FIG. 15B is a schematic view of a bladder according to an aspect of the present invention.

For example, in FIGS. 15A and 15B, bladder 20 is shown schematically. In FIG. 15A, the total work or energy input into bladder 20 is equal to AUC MVE during the filling of the bladder 20 on the left side of line 120. This assumes no or relatively little detrusor contractions occur, or, line 10 in FIG. 4 may be used to calculate the AUC MVE prior to line 120. Likewise in FIG. 15B, the energy power is equal to MVC DE plus MVC MVE on the right side of line 90. Under the first law of thermodynamics (and excluding heat energy as negligible), AUC MVE on both sides of line 90 should be equal. Essentially, this would be equivalent to stretching and releasing a spring or expanding and contracting a balloon.

By subtracting out AUC MVE calculated on the left side of line 90 or line 120 from the total AUC under line 76 on the right side of line 90, the detrusor contribution is isolated from the total energy on the voiding side. Therefore, when attempting to quantify values representative of underactive bladder, variances based on patient physiology may be removed and result in a more consistent value and analysis. For example, an elderly woman with a normal bladder would likely exhibit lower vesicoelastic characteristics than a young male. As such, the power and work is calculated on the left side of line 90 can then be subtracted from the power or work calculated for the right side of line 90 for the elderly woman and results in simply the detrusor contractility that may be more consistent across all patients (young, old, male, female). The result is a more standardized means of determining a healthy or unhealthy bladder.

Figure 13:
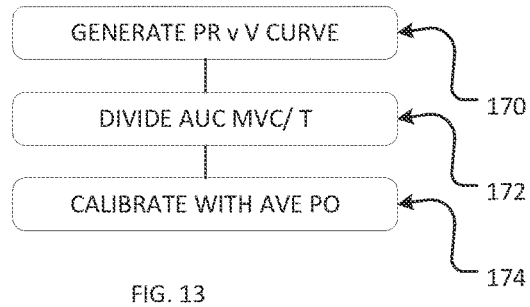
FIG. 13 is a flowchart according to an aspect of the present invention.

In FIG. 13, a process for utilizing the above approach is described. In FIG. 13, step 70 in FIG. 6 begins by generating the pressure versus volume curve as described in aforementioned embodiments in step 170. The AUC MVE is then calculated for the left side of line 90 or line 120. In step 172, the AUC MVE is then divided by the amount of time during fill. This represents total work done during the fill stage W=dW/dT. From this, it can be assumed that the average power on the void side due to vesicoelastic conditions should be the same. Accordingly, when the power curve of FIG. 12B is generated, this average power is subtracted from each point along the power curve from line 90 until voiding is complete in step 174. By this way, a calculation of the true power caused by the detrusor is determined.

Figure 14:
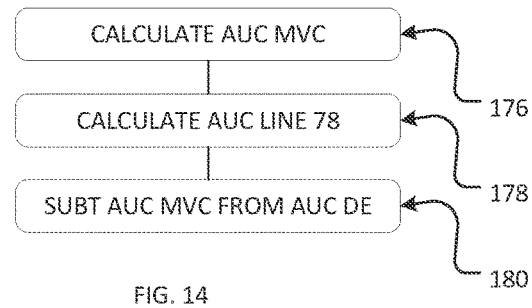
FIG. 14 is a flowchart according to an aspect of the present invention.

With reference to FIG. 14, another embodiment is shown and described. Here, the pressure versus volume curve is calibrated based on the amount of work calculated during the filling phase. In FIG. 14, the process starts at step 176 where the AUC MVE is calculated. In step 178, the total AUC under line 78 is calculated. In step 180, instead of using the AUC MVE calculated underlines 12 and 14, the AUC calculated in step 176 is subtracted from AUC under line 78 to arrive at the AUC DE.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A method performed by at least one processing device and at least one memory device and at least one interactive user interface for use on a display for analyzing data from a urodynamic study, the method comprising:

determining pressure data from individual pressure values from said urodynamic study that represents a pressure of liquid inside a bladder during a fill operation or a void operation, and storing said pressure data in said memory device;

determining volume data from the urodynamic study that represents a volume of said liquid inside said bladder and storing said volume data in said memory device;

using said processing device to correlate said pressure data with said volume data to form a pressure vs volume curve;

displaying the pressure vs volume curve through the user interface;

employing a linear regression to identify a best fit line to the pressure vs volume curve;

adjusting the best fit line to provide an adjusted best fit line that resides at points of the pressure vs volume curve that represents vesicoelastic characteristics of a bladder; and displaying the adjusted best fit line with the pressure vs volume curve on a same graph to display a separation line between a detrusor function and an elastic bladder function.

2. The method according to claim 1, further comprising:
presenting the adjusted best fit line in an interoperable fashion that allows a user to adjust the best fit line manually to the pressure vs volume curve.

3. The method according to claim 2, further comprising:
providing a plurality of points distributed along the adjusted best fit line;
wherein each of the plurality of points is selectably movable to drag a portion of the adjusted best fit line.

4. The method according to claim 2, further comprising:
calculating with said processing device an amount of detrusor work performed by said bladder by determining an area between said adjusted best fit line and the pressure vs volume curve;
calculating with said processing device an amount of vesicoelastic work performed by said bladder by determining an area under said adjusted best fit line; and
displaying said detrusor work and said vesicoelastic work through the user interface.

5. The method according to claim 1, further comprising:
calculating with said processing device an amount of detrusor work performed by said bladder by determining an area between said adjusted best fit line and the pressure vs volume curve;
calculating with said processing device an amount of vesicoelastic work performed by said bladder by determining an area under said adjusted best fit line; and
displaying said detrusor work and said vesicoelastic work through the user interface.

6. The method according to claim 1, further comprising:
identifying a micturition starting point in the pressure data and the vesicoelastic pressure data by identifying a peak pressure; and
displaying the micturition starting point through the user interface.

7. The method according to claim 6, further comprising:
presenting the micturition starting point as an interactive component presented through the user interface;
wherein the micturition starting point is movable to adjust the micturition starting point.

8. The method according to claim 7, further comprising:
calculating with said processing device an amount of detrusor work performed by said bladder by determining an area between said adjusted best fit line and the pressure vs volume curve up until the micturition starting point;

calculating with said processing device an amount of vesicoelastic work performed by said bladder by determining an area under said adjusted best fit line up to the micturition starting point; and displaying said detrusor work and said vesicoelastic work through the user interface.

9. The method according to claim 6, further comprising: identifying a voiding end point calculating with said processing device an amount of detrusor work performed by said bladder by determining an area between said adjusted best fit line and the pressure vs volume curve after the micturition starting point and to the voiding end point;

calculating with said processing device an amount of vesicoelastic work performed by said bladder by determining an area under said adjusted best fit line from the micturition starting point to the voiding end point; and displaying said detrusor work and said vesicoelastic work through the user interface.

10. The method according to claim 1, further comprising comparing the detrusor work against a standard value to determine whether a condition of overactive bladder exists.

11. The method according to claim 1, wherein the best fit line is adjusted by identifying relatively lower points of the pressure vs volume curve and filtering abnormal spikes.

12. A computing device for analyzing data from a urodynamic study, the device comprising:

a memory device configured to store pressure data and volume data taken from said urodynamic study that represents a pressure of liquid and a volume of liquid inside a bladder during a fill operation or void operation;

a processing device configured to retrieve said pressure data from said memory device and using said processing device to correlate said pressure data with said volume data to form a pressure vs volume curve, wherein the processing device is further configured to employ a linear regression to identify a best fit line to the pressure vs volume curve and adjust the best fit line to provide an adjusted best fit line that resides at points of the pressure vs volume curve that represents vesicoelastic characteristics of a bladder;

a user interface that displays the pressure vs volume curve through the user interface and displays the adjusted best fit line on a same graph as the pressure vs volume curve to identify a separation line between the vesicoelastic characteristics of a bladder and detrusor characteristics of the bladder.

13. The computing device to claim 12, wherein the user interface presents the adjusted best fit line in an interoperable fashion that allows a user to adjust the best fit line manually to the pressure vs volume curve.

14. The computing device to claim 13, wherein the user interface provides a plurality of points distributed along the adjusted best fit line that are selectably movable to drag a portion of the adjusted best fit line.

15. The method according to claim 13, wherein:

the processing device is further configured to calculate an amount of detrusor work performed by said bladder by determining an area between said adjusted best fit line and the pressure vs volume curve;

the processing device is further configured to calculate an amount of vesicoelastic work performed by said bladder by determining an area under said adjusted best fit line; and the user interface is further configured to display said detrusor work and said vesicoelastic work.

16. The computing device to claim 12, wherein:

the processing device is configured to calculate an amount of detrusor work performed by said bladder by determining an area between said adjusted best fit line and the pressure vs volume curve;

the processing device is configured to calculate an amount of vesicoelastic work performed by said bladder by determining an area under said adjusted best fit line; and the user interface is configured to display said detrusor work and said vesicoelastic work.

17. The computing device according to claim 12, wherein the processing device is configured to identify a micturition starting point in the pressure data and the vesicoelastic pressure data by identifying a peak pressure; and the user interface is configured to display the micturition starting point.

18. The computing device according to claim 17, wherein the user interface is configured to:

present the micturition starting point as an interactive component presented through the user interface;

present the micturition starting point is movable to adjust the micturition starting point.

19. The computing device according to claim 18, wherein:

the processing device is configured to calculate an amount of detrusor work performed by said bladder by determining an area between said adjusted best fit line and the pressure vs volume curve up until the micturition starting point;

the processing device is configured to calculate an amount of vesicoelastic work performed by said bladder by determining an area under said adjusted best fit line up to the micturition starting point; and the user interface is configured to display said detrusor work and said vesicoelastic work.

20. The computing device according to claim 17, wherein:

the processing device is configured to identify a voiding end point the processing device is configured to calculate an amount of detrusor work performed by said bladder by determining an area between said adjusted best fit line and the pressure vs volume curve after the micturition starting point and to the voiding end point;

the processing device is configured to calculate an amount of vesicoelastic work performed by said bladder by determining an area under said adjusted best fit line from the micturition starting point to the voiding end point; and the user interface is configured to display said detrusor work and said vesicoelastic work.

* * * * *